(12) United States Patent
Villax et al.

(10) Patent No.: US 8,109,267 B2
(45) Date of Patent: Feb. 7, 2012

(54) SIMPLE INHALER

(75) Inventors: Peter Villax, Lisbon (PT); Iain Grierson Mcderment, Hertfordshire (GB); Martin Bunce, Wiltshire (GB)

(73) Assignee: Hovione International Ltd., Wanchai (HK)

(*) Notice: Subject to any disclaimer, the term of this patent is extended or adjusted under 35 U.S.C. 154(b) by 671 days.

(21) Appl. No.: 12/299,922

(22) PCT Filed: May 11, 2007

(86) PCT No.: PCT/GB2007/001756
§ 371 (c)(1),
(2), (4) Date: Nov. 7, 2008

(87) PCT Pub. No.: WO2007/132217
PCT Pub. Date: Nov. 22, 2007

(65) Prior Publication Data
US 2009/0178676 A1  Jul. 16, 2009

(30) Foreign Application Priority Data
May 16, 2006 (PT) ........................ 103.481

(51) Int. Cl.
*A61M 15/00* (2006.01)
*A61M 15/08* (2006.01)
*A61M 16/00* (2006.01)
*A61M 16/10* (2006.01)
*B05D 7/14* (2006.01)
*B65D 83/06* (2006.01)

(52) U.S. Cl. .......... 128/203.15; 128/203.12; 128/203.23

(58) Field of Classification Search ............. 128/200.14, 128/200.21–200.24, 200.27, 203.12, 203.15, 128/203.19, 203.21, 203.23; 604/58; *A61M 15/00, 15/05, 16/00, 16/10; B05D 7/14, 83/06*
See application file for complete search history.

(56) References Cited

U.S. PATENT DOCUMENTS
4,524,769 A  6/1985  Wetterlin
(Continued)

FOREIGN PATENT DOCUMENTS
EP  1504781  2/2005
(Continued)

OTHER PUBLICATIONS

Hovione—Dry powder Inhalers, visited Sep. 27, 2011, http://www.hovione.com/twincaps/twincaps.asp.*

(Continued)

*Primary Examiner* — Loan Thanh
*Assistant Examiner* — Oren Ginsberg
(74) *Attorney, Agent, or Firm* — Dickstein Shapiro LLP

(57) ABSTRACT

A dry powder inhaler for pulmonary or nasal use, comprising at least an inhaler body and a cartridge with one or more compartments each containing one dose of a drug. The compartment has holes to admit air and holes to deliver powder, which, in use, communicate with an inhalation channel in the inhaler body. To prevent the powder from leaking through the compartment holes before use, the air admission holes are of reduced dimension, thereby blocking or hindering powder exit under the force of gravity. When the cartridge is inserted inside the inhaler body, all its holes can be blocked. By sliding the cartridge in relation to the body until the inhalation position is reached, the holes come into in fluid communication with one another and with the inhalation channel, thereby allowing a flow of air to disperse and entrain the dose through the mouthpiece. Five embodiments are disclosed.

27 Claims, 7 Drawing Sheets

U.S. PATENT DOCUMENTS

| | | | |
|---|---|---|---|
| 4,889,114 A | 12/1989 | Kladders | |
| 5,042,472 A | 8/1991 | Bunin | |
| 5,048,514 A * | 9/1991 | Ramella | 128/203.21 |
| 5,239,991 A | 8/1993 | Chawla et al. | |
| 5,301,666 A | 4/1994 | Lerk et al. | |
| 5,349,947 A * | 9/1994 | Newhouse et al. | 128/203.21 |
| 5,372,128 A * | 12/1994 | Haber et al. | 128/203.21 |
| 5,533,505 A | 7/1996 | Kallstrand et al. | |
| 5,575,280 A | 11/1996 | Gupte et al. | |
| 5,595,175 A | 1/1997 | Malcher et al. | |
| 5,647,349 A * | 7/1997 | Ohki et al. | 128/203.15 |
| 5,651,359 A | 7/1997 | Bougamont et al. | |
| 5,660,169 A | 8/1997 | Kallstrand et al. | |
| 5,715,811 A * | 2/1998 | Ohki et al. | 128/203.21 |
| 5,797,392 A | 8/1998 | Keldmann et al. | |
| 5,829,434 A | 11/1998 | Ambrosio et al. | |
| 5,918,594 A | 7/1999 | Asking et al. | |
| 6,098,619 A | 8/2000 | Britto et al. | |
| 6,102,035 A | 8/2000 | Asking et al. | |
| 6,105,574 A | 8/2000 | Jahnsson | |
| 6,116,239 A * | 9/2000 | Volgyesi | 128/203.15 |
| 6,286,507 B1 | 9/2001 | Jahnsson | |
| 6,332,461 B1 | 12/2001 | Hyppola | |
| 6,575,160 B1 * | 6/2003 | Volgyesi | 128/203.15 |
| 6,810,872 B1 * | 11/2004 | Ohki et al. | 128/203.15 |
| 7,032,593 B2 | 4/2006 | Johnston et al. | |
| 7,278,982 B2 * | 10/2007 | Tsutsui | 604/58 |
| 7,353,823 B2 * | 4/2008 | Tsutsui | 128/203.21 |
| 7,722,566 B2 * | 5/2010 | Tsutsui | 604/148 |
| 7,806,117 B2 * | 10/2010 | Tsutsui | 128/203.21 |
| 7,832,399 B2 * | 11/2010 | Ganem et al. | 128/203.21 |

FOREIGN PATENT DOCUMENTS

| | | |
|---|---|---|
| FR | 2 278 352 | 2/1976 |
| GB | 1182779 | 3/1970 |
| GB | 2064336 | 6/1981 |
| GB | 2178965 | 2/1987 |
| WO | WO-99/36116 | 7/1999 |

OTHER PUBLICATIONS

International Search Report for PCT/GB2007/011756 dated Sep. 13, 2007.

* cited by examiner

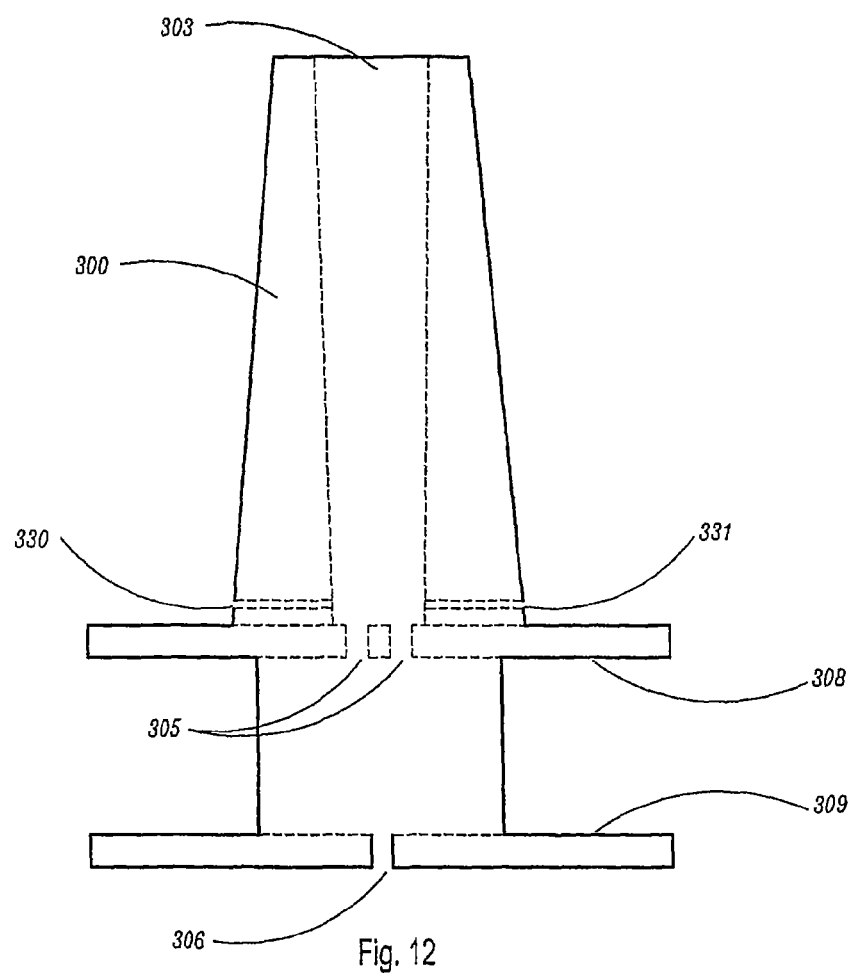
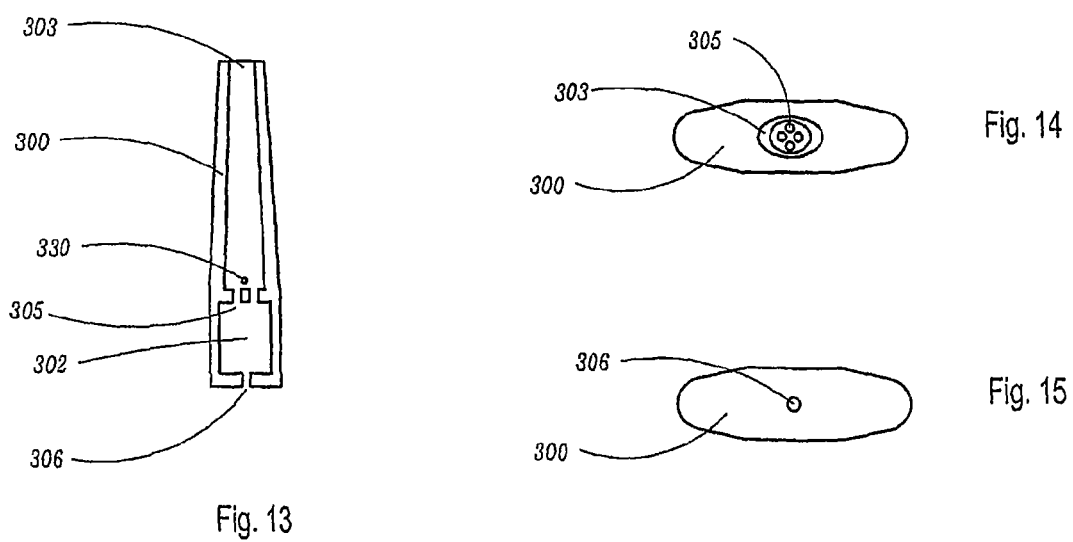

SIMPLE INHALER

The present invention describes a pulmonary or nasal inhaler of simple construction and operation.

Inhalers used for the delivery of pharmaceutical compounds are widely known, becoming widespread after the development of the dosing valve and pressurized metered dose inhaler by Charles Thiel in 1956, and the introduction of several dry powder inhalers, which started in the 1960s and continues to this day.

These inhalers have been used chiefly in the treatment of diseases such as asthma and chronic obstructive pulmonary disease, but recently applications have been developed to deliver drugs systemically via the lung or nose.

The quest to combine efficacy, ease of use, convenience and small size have dominated these efforts. Early devices made use of capsules (GB 1,182,779, Spinhaler; GB 2 064 336, Rotahaler; U.S. Pat. No. 4,889,114, Inhalator; and FR 75 21844, Cyclohaler). but capsules require dexterity in handling, which is a matter of inconvenience, and adds to the cost. Many also possess a cutting or piercing or opening mechanism, in most cases necessitating the use of metal needles or blades (PT 101.450 FlowCaps), yet another source of cost. Ways of avoiding capsule handling can be found in U.S. Pat. No. 5,595,175 and U.S. Pat. No. 5,651,359, but the method by which this has been achieved has brought more mechanical complexity and therefore higher cost.

In situations where an infectious agent is being treated or is simply present in the mouth and airways, there is the need to eliminate the possibility of inhaler contamination and to this end it is highly advantageous to have a sufficiently economic device so that it may be used once and disposed of. Indeed, inhalers to treat viral diseases such as influenza effectively are known (GB 2 178 965 Diskhaler), but the inhaler requires to be re-loaded and re-used over the entire length of the five-day treatment, being repeatedly contaminated with the virus. Moreover, the great majority of influenza patients are inhaler-naive, requiring that the device be of extreme simplicity and intuitive to use.

Consequently, significant attention has been given to disposable devices, and very economical designs have appeared in the literature. A recurring challenge for inventors has been the need to segregate the powder dose so as to prevent it from spilling out prior to use. In one design, no less than six patents (U.S. Pat. No. 5,533,505, U.S. Pat. No. 5,660,169, U.S. Pat. No. 5,918,594, U.S. Pat. No. 6,102,035, U.S. Pat. No. 6,105,574 and U.S. Pat. No. 6,286,507) have been granted for the same device, describing various mechanisms by which the powder dose might be packaged inside the device. This is not difficult in itself, but is a source of cost and industrial or operational complexity, all factors to be avoided.

U.S. Pat. No. 7,032,593 describes also a simple device containing a dose of powder, which is protected against leakage by means of a tether or film strip which is removed immediately prior to use; but in this and in another embodiment in the same patent, the very fine and freely flowing powder does not appear to be prevented from flowing out through the ventilation holes of the device, immediately prior to inhalation.

Moreover, disposable devices have often failed to address the inhaler's most important function, which is to disperse agglomerates of drug particles and excipients down to their original, inhalable size of less than 5 µm. One of the simplest designs of all uses a simple straw (U.S. Pat. No. 5,797,392, DirectHaler), but the fact that the dispersion and entrainment of the dose occur simultaneously in a very short period of time—a fraction of one second—may reduce the efficiency of the device and result in a lower dose being deposited in the lung. Other very simple devices without apparent powder dispersion features include U.S. Pat. No. 5,042,472, U.S. Pat. No. 5,239,991 and U.S. Pat. No. 6,098,619. A lower efficiency may dictate the need to increase the drug dose to achieve the desired therapeutical effect. In addition, fast delivery means that the entire dose is delivered suddenly and this may cause the "powdery mouth" effect. Neither of these characteristics are desirable.

While asthma inhalers were typically designed to hold a large number of pre-metered or device-metered doses of potent drugs, they were largely unsuited for the delivery of large doses. Pre-metered devices are also to be preferred, as device-dispensed doses have been prone to dose metering variability. Devices using a cup as a metering device included in a sliding mechanism are known (U.S. Pat. No. 4,524,769 Turbuhaler, U.S. Pat. No. 5,575,280 Clickhaler; U.S. Pat. No. 5,829,434 Twisthaler, U.S. Pat. No. 6,332,461 Easyhaler) but they are unsuited to metering large doses, and their function is to measure and transport a dose from a bulk powder reservoir to the mouthpiece channel.

There is therefore a need for an inhaler that is pre-filled with unit doses of powder, for patient convenience; disposable, for reasons of safety and hygiene; simple, for economic reasons and ease of use; and with a high dispersive and entrainment efficacy, for therapeutic benefit.

The present invention is directed to a dry powder inhaler which seeks to combine all of these characteristics and advantages.

The dry-powder inhaler of the present invention is intended for pulmonary or nasal delivery, and includes an inhaler body composed of a mouthpiece or nosepiece and an opening in the body. The inhaler has a body front inlet which allows fluid communication between the mouthpiece and the opening in the body and also includes a powder cartridge mounted in the opening of the inhaler body. The powder cartridge has at least one powder compartment and it is designed to move inside the opening, the inhaler body preferably having means to hold the cartridge in place in the opening and means to limit the amount of travel the cartridge can move inside the opening. Each powder compartment has a compartment front inlet and the cartridge can move inside the opening from a first position, in which the compartment front inlet is offset from the mouthpiece passage, to a second position in which the compartment front inlet is aligned with it. In the first position, there is no fluid communication and the powder inside a cartridge compartment is isolated from the mouthpiece and cannot flow out. In the second position, the cartridge has been moved to a point where a compartment front outlet is aligned with the mouthpiece, thereby defining a dispersion chamber from which the contents of the powder chamber can be delivered to the mouthpiece. This construction results in considerable economic savings, as there is no need to employ storage chambers which are distinct from dispersion chambers. The combination of two components forming a dispersion chamber is an inventive feature of the present invention. Avoiding the storage of powder in one chamber and its dispersion in another, has other technical advantages, namely that losses in transferring the powder from one chamber to another are also avoided and that the surface area where powder might adhere and fail to be properly dispersed and entrained, is reduced. Another advantage is that the user does not have to handle unit doses.

(In the following description, "proximal" refers to points on the inhaler that are closer to the mouth or nose and "distal" to points that are farther; and references to "mouthpiece" include "nosepiece").

In order for a powder compartment to become a dispersion chamber, air must be admitted to it. In the inhaler of the present invention, the inhaler body further includes a body rear inlet, which extends from the inhaler body to the body opening and each powder compartment includes a compartment rear inlet. Furthermore, we have provided the inhaler body with a body front inlet, which is located on the inhaler body, at the distal end of the mouthpiece channel, and with body side inlets, which admit air directly from the atmosphere to the mouthpiece channel and supplement the volume of air crossing the powder compartment. The body side inlets should desirably enter the mouthpiece channel as close as possible to the body front inlet, so as to create turbulence on its surface and avoid any unwanted powder accumulation.

When a powder compartment is in the second position as described above, air is able to travel through the body rear inlet, into the compartment rear inlet, through the compartment, out of it through the compartment front inlet, past the body front inlet, into the mouthpiece channel and finally out of the inhaler. When this flow is established as a result of suction on the mouthpiece and a dose of a pharmaceutical powder is contained inside the compartment, the flow of air will induce turbulence leading to a break up of powder agglomerates and to a dispersion of the particles, for entrainment and final deposition in the intended site, in lung or in the nasal cavity, depending on the application.

This inhaler does not use conventional pharmaceutical capsules, such as gelatine or cellulose/HPMC capsules. Rather, the powder doses are contained inside compartments which are shaped like a capsule. Although other shapes are possible, the rounded extremities of a capsule and its cylindrical, constant section make this shape highly suited to minimize powder retention during and after inhalation. In fact any shape with an absence of sharp angles, such as spherical, oval, frusto-conical, bi-conical and the like would be equally advantageous.

The powder compartments, of which there can be just one or multiple depending on the application, but of which there are preferably one or two, are built, shaped, drilled or moulded inside a cartridge. Thus one single component, which can be manufactured in a single step if by injection moulding, contains the powder compartment or compartments. Whatever the number of powder compartments, it is understood that they are always isolated from each other and that there is no communication between them. Such a cartridge containing two powder compartments is a further inventive feature of the present invention.

The inhaler body and the powder cartridge can be made of any suitable material for pharmaceutical use, but plastics are to be preferred, and the material used for the cartridge should advantageously be transparent.

Whatever the material chosen, both the inhaler body and the powder cartridge should be compatible with the powder intended to be contained and delivered, so as to minimize degradation of the powder by chemical reaction and to reduce powder retention during storage and delivery. To this end several plastics have been tested, namely polypropylene, Nylon, transparent Nylon, amorphous Nylon, Acetyl (POMP): Ultra form N2320, Polyester (PET), K-resin, Polyethylene (LDPE): Riblene MVlO, Acetal and others. Results show the plastic grade must be carefully adjusted to the powder used and no material can be identified as being universally appropriate. Moreover, these materials have varying degrees of transparency, and sometimes a trade-off must be made between transparency and powder adhesion minimization.

The powder cartridge has inlets to allow air to travel into a powder compartment, disperse the powder, entrain it into the mouthpiece and out into the patient's mouth. However, the compartment rear inlet, located on the distal air admission side of a powder compartment needs to be very small, so that immediately after filling with powder and before the cartridge unit is inserted into the inhaler body, the powder does not flow out of the compartment rear inlet under the force of gravity. We prefer to make these rear inlets as a narrow slit, one per powder compartment, though the same function could be achieved with several very small round holes, of a diameter of 1 mm or less. However a slit is easier to manufacture by injection moulding, and we prefer each slit width to be 1 mm or less, as we have found that this dimension can block or substantially hinder the flow of powder out of the compartment.

Whether using a slit or a small hole as a shape for the compartment rear inlet to admit air to the powder compartment, we have found that tapering the walls of the slit or hole in the direction of the compartment further promotes the blocking of the powder. Such a tapering creates a funnel space directly above the compartment rear inlet and we have found that the best taper angle to block the powder is included between 179° and the angle of repose of the powder contained in the powder compartment, and preferably between 120° and the angle of repose of the powder. This funnel blocks powder flow under gravity by promoting the bridging of particles above the funnel and is a further inventive feature of the present invention.

Conversely, the compartment front inlet, situated at the proximal end of the powder compartment needs to be sufficiently wide to allow normal filling and high-speed filling of the powder. Usually, this compartment front inlet will be of the same diameter as the powder compartment itself. This means that during filling the powder cartridge is desirably held in the same orientation, compartment rear inlets pointing down to the ground, and compartment front inlets pointing up.

Immediately after filling a powder compartment or compartments with a unit dose of powder, desirably in a factory automated environment, the powder cartridge must be inserted into the inhaler body, which is preferably built so that the compartment front and rear inlets are in contact with a continuous, smooth surface on the inhaler body and the contact is a close tolerance fit with the front wall and the rear wall of the inhaler body where that contact takes place. In the storage position, when the powder compartment is offset from the body front and rear inlets air inlets and from the mouthpiece channel, the powder unit dose is effectively sealed inside its compartment, as the cartridge is held between the front wall and the rear wall of the inhaler body. This close contact with the walls of the inhaler body prevents the powder from leakage during storage and this is a further inventive feature of the present invention. At this point the inhaler is ready for packing, desirably in a foil or aluminium pouch, or pouch or packaging of any other suitable material and under low or equilibrium humidity conditions.

Another method to ensure that the powder does not leak out of the powder compartments during storage or manipulation is to construct the powder cartridge with protruding circular rims around the powder compartment front inlets. In this construction, the close contact will be between the circular rims of the powder compartments and the inhaler body. This is to be preferred, as the contact surface will be minimized and thus the tolerance of the fit between the cartridge and the inhaler body can even be closer than in the previous construction, but without causing such a level of friction that would require excessive force to push the powder cartridge into position for inhalation.

Moreover, the powder cartridge can be constructed from a softer material, more compressible than that of the inhaler body, so that the circular rims of the powder compartments, when coming into contact with the harder material of the inhaler body will be subjected to a compression force due to the close fit, and slightly change shape, becoming wider as they are compressed, thus offering a greater contact surface area and better protection against powder leakage.

Finally, powder leakage can be further ensured by blocking the powder cartridge inside the inhaler body, so that even if the inhaler is subjected to strong vibration during transport, no powder will be lost. This can be achieved in several ways: either shrink-wrapping the packaging pouch around the inhaler, or inserting the inhaler into a rigid packaging shell, or using an adhesive tape around the inhaler body and powder cartridge or using a locking feature moulded into inhaler body and/or the powder cartridge. The pouch or the adhesive tape methods have the added benefit of being tamper-evident systems, which are useful in once-only use, disposable inhalers such as the present one.

In addition to preventing the powder from leaking under gravity, the inlets on the powder compartment as well as those on the inhaler body play an important role in the function of this inhaler, as their diameter and surface areas and their position determine the aerodynamic profile of the device and this in turn determines the comfort with which the user inhales, and the efficacy of the device.

In the case of the present invention, the source of power for powder dispersion and entrainment is the patient's inspiratory flow and this has to be used as efficiently as possible by the inhaler. Such devices, known as passive inhalers, do not need motors or other complex mechanical features to operate, but on the other hand tend to be dependent on the airflow rate: the higher the flow, the better the dispersion and the entrainment and the higher the lung dose. This is undesirable, as the same patient inhaling a different flow rates will obtain variable doses. Accordingly, the development of an inhaler which reaches close to its maximum efficacy at a relatively low flow rate has been a major goal in inhalation technology.

When a powder compartment is in fluid communication with various inhaler inlets, i.e. when it is the inhalation position, air and powder are able to mix and flow out of the inhaler. The function of the body side inlet or inlets is very important here, supplementing the small amount of whatever air is able to penetrate the powder compartment through the narrow slits or small holes of the compartment rear inlet. These body side inlets allow for the inhalation to be comfortable and for the powder/air ratio to be desirably lean in powder and rich in air, thus maximizing the entrainment capability of the air.

With the provision of the body side inlet, the user can comfortably generate a pressure drop of 4 kPa, which is recognized in the pharmacopoeias as a suitable pressure drop from a user point of view, as this is half of the maximum pressure drop that the intercostal muscles and the diaphragm can generate. In the case of the nose, the pressure drop that can be generated is lower (because the resistance to the passage of air in the nasal cavity is higher) and in this case one only needs to change the diameter and number of body side inlets to regulate the ideal pressure drop for a nasal delivery.

Now if the user can apply a considerable suction to the mouthpiece, it is important to avoid a powder exit that is too rapid. This is the function of the configuration of the compartment rear and front inlets, particularly in the way their dimensions can be varied to regulate the flow of air which enters and leaves the inhaler.

So, in addition to avoiding the leakage of powder under gravity, the slits or holes of the compartment rear inlet restrict the admission of air. By experimentation of different slit lengths, or number of small holes, it is possible to tune the inhaler to deliver one dose of powder in the desired length of time, given a constant flow rate. The duration can thus be varied between about 200 milliseconds to several seconds. However we prefer to regulate the lengths of the slits or number of holes to give the user a powder delivery time which is longer than 0.5 second and preferably up to 2 seconds at a flow rate of 35 L/min"1, so that there is an excess of air to transport the powder, reduce the "powdery mouth" feeling and improve lung deposition. At the stated flow rate, the delivery duration of 2 seconds will result in an inhalation volume of 1.2 litres of air. Since a person inhaling through an inhaler uses about 2 litres of air for a complete inhalation (it can be more), this means that there is still about 0.8 litre of air to chase the powder dose deep into the lung. For nasal applications, it is desirable to have a shorter delivery duration.

The size and configuration of the body front inlet also have a regulating effect on airflow. In their absence, powder delivery out of the compartment front inlet, which is very wide, would be far too rapid and result in perhaps insufficient dispersion. Thus the body front inlet acts as further barrier to the path of the powder and is therefore advantageously provided, as it slows down the delivery and offers a final obstacle to the particles, assisting in their dispersion. This barrier is preferably provided in the form of several small perforations right at the entrance of the mouthpiece channel, though other shapes can be used as well. The powder storage chamber is now fully transformed into a dispersion chamber, inside the same compartment, which is now facing the perforated barrier of the front body inlet.

Notwithstanding the preferred construction of several perforated holes, industrial considerations may determine the moulding of one or two longitudinal slits in the inhaler body front inlets instead, but with a surface area identical or similar to that of the multiple perforations.

The combination of a restricted flow of air at the air admission side of the compartment and the restrictions at its exit caused by the inhaler body inlet, causes the inhalation flow to be more prolonged and in a delivery desirably more gradual, reducing the "powdery mouth" effect and improving pulmonary deposition. This combination of small holes in the dispersion chamber and an additional inlet downstream of the dispersion chamber have been described in PT 101,450 and are incorporated herein by reference.

With this aerodynamic profile, the compartment is an efficient dispersion chamber. Particles may become further dispersed down the mouthpiece inhalation channel, but the highly turbulent and gradual dispersion of the powder is actually observable inside the compartment, when this is manufactured of a transparent material. A storage chamber which becomes a dispersion chamber, the dispersion chamber being defined by elements situated on different mechanical components which are combined at the time of inhalation, is a further inventive feature of the present invention.

The holes that admit air into the inhaler body from the atmosphere, such as the body rear inlet and body side inlet should preferably be protected against inadvertent blocking, as could easily happen if covered with the patient's finger. We prefer to construct these holes with means to prevent such blockage. For instance, the perimeter of the holes can have crenellations, so that even if covered by a finger, air will be able to flow through the gaps. Other constructions are possible, such as features in the inhaler components which result in air gaps that are narrower than a finger but longer than one fingerprint, so that blocking of air is impossible. Means to prevent the blocking of the admission of air to the inhaler body are an inventive feature of the present application.

When the patient wishes to use the inhaler of the present invention, he or she removes it from its packaging. The container is now in its storage position. The patient now moves the container to the first inhaler position, and at this point the compartment has its rear inlet aligned with the body rear inlet, that is the powder could again leak under the force of gravity. The slits or small holes have thus a further function, as they prevent the powder from leaking under gravity, which would be obviously undesirable. The patient inhales the first dose, according to the instructions for use. If there is a second compartment, the patient moves it to the inhalation position and inhales a second time, repeating the maneuvre as often as there are compartments.

The inhaler of the present case can have several embodiments and those that are now described all constitute inventive features of the present application.

In a first embodiment, the powder cartridge is a tray which is inserted sideways into the inhaler body and is pushed transversally, so that a powder compartment becomes aligned with the mouthpiece channel and inhalation may take place (the Tray model). If the powder cartridge includes a second powder compartment, the patient continues to advance the cartridge in the same direction until the second compartment is also aligned for inhalation to take place. The direction of the movement of the cartridge can be perpendicular to the longitudinal axis of the inhaler body and of the mouthpiece channel, but it could be at another angle, different from a right angle, provided the longitudinal axis of the powder compartment in movement is substantially parallel to that of the mouthpiece channel.

In another embodiment which is a variation of the first, the powder cartridge is composed of not one, but two separate trays, each tray containing one powder compartment (the Split Tray model). Here, one cartridge can be pushed from one side towards the central inhalation position where it can be inhaled, and then the second cartridge can be pushed from the other side, in a contrary direction, displacing the first cartridge which is now empty, occupying the central inhalation position and being inhaled in turn.

A third embodiment of the present invention (the Shuttle model) combines the advantages of the Tray and Split Tray Models, employing a single cartridge moving bi-directionally. Here, the powder cartridge, containing at least one powder compartment, has the same tray shape, but instead of moving in a single direction, it is moved in a first direction towards the central inhalation position where the first powder compartment can be inhaled, and then in the contrary direction so that the second powder compartment may in turn be inhaled.

In a fourth embodiment of the present invention, the powder cartridge is a cylinder which comprises at least one powder compartment, the or each compartment being parallel to the cylinder (and to each other if multiple compartments are present) and in this case a powder compartment is brought into alignment with the mouthpiece channel by rotating the cylinder (the Cylinder model). Here the plane of rotation of the powder cartridge is substantially perpendicular to the longitudinal axis of the inhaler body and mouthpiece channel.

In a fifth embodiment of the present invention, the powder cartridge is a disk which comprises one, two or more powder compartments radially extending from the centre of the disk and in this case a powder compartment is brought into alignment with the mouthpiece channel by turning the disk-shaped powder cartridge (the Disk model). In this case the plane of rotation of the powder cartridge is substantially parallel to the longitudinal axis of the inhaler body and mouthpiece channel.

In all embodiments, in the initial storage position, the powder unit dose is contained in each of the compartment or compartments and in this position the powder is sealed by the contact with the inhaler body walls. When a cartridge is moved and a powder compartment is in the inhalation position, all inlets of the several embodiments are in fluid communication and the suction applied to the mouthpiece causes the powder to become aerosolized and to become entrained into the mouth or nose. In the case of a nasal application, the inhalation channel will ideally comprise a branching off and two symmetrical ends, shaped to fit the nostrils, thus allowing the dose to be inhaled simultaneously by both nostrils.

In the Tray model, the patient can advantageously be informed that the powder cartridge has been advanced to the inhalation position by provision of a mechanical detent, a clicking sound or the like. In the Shuttle, Split Tray, Cylinder and Disk models, there is no need for a mechanical detent as the devices can be easily built with a mechanical feature on the inhaler body or in the cartridge which blocks the sliding or rotation of the cartridge at the precise point where inhalation will take place, so that the user only has to move the cartridge to a point where it comes to a hard stop. This is a further inventive feature of the present invention and is great importance, particularly in indications where patients are not familiar with inhalation, and need to be successful on their very first attempt to use the inhaler.

Tray, Shuttle, Cylinder and Disk models require at least two components, while the Split Tray model requires at least three components. Inhalers using two components only where a factory metered dose powder is included and held in place without leaking by the disposition of the two components, which can be altered at the time of inhalation to allow fluid communication and inhalation to take place, while still preventing unwanted powder leaking, is a further inventive feature of the present invention.

All five embodiments are easy to use, as a single movement of a powder cartridge is sufficient to bring a powder compartment in alignment with the mouthpiece channel and this is an important advantage for the inhalers of this invention. Achieving operation with a single movement of inhaler parts when it consist of at least two components is an inventive feature of the present application.

All of these five embodiments comprise the inventive features detailed in the present application and the person skilled in the art will be able to apply the same teachings to other inhalers so these descriptions in no way limit the invention to the embodiments described.

In order that the invention may be well understood, there will now be described some embodiments thereof, given by way of example, reference being made to the accompanying drawings, in which:

FIG. 12 is a longitudinal section of a third embodiment of the invention in the form of a Shuttle model;

FIG. 13 is a transversal section of the Shuttle model;

FIGS. 14 and 15 are front and rear elevations, respectively, of the Shuttle model;

Figure 1:
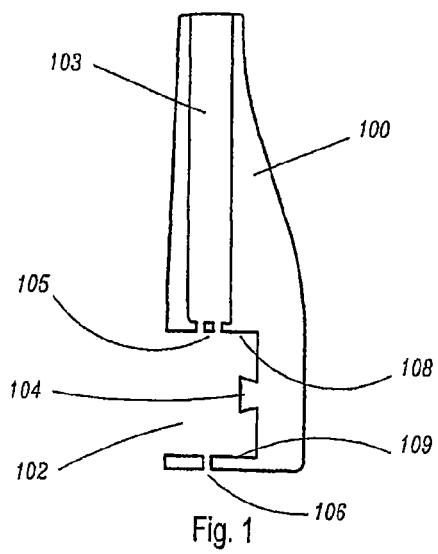
FIGS. 1 and 2 are longitudinal sections of a first embodiment of the invention in the form of a Tray model.

Referring to the drawings, numbered sequentially after the word "Fig.", like numerals indicate like parts, and each of the five embodiments is identified with series of numbers where the number of hundreds is the number of the embodiment (1xx to 5xx) and the equivalent feature in each of the embodiments has the same number xx.

There is shown in FIG. 1 a first embodiment of the invention, hereinafter referred to as the Tray model, comprising an inhaler body 100 having an opening 102, a mouthpiece 103, air inlets 105; 106 in the inhaler body, a front wall 108 and a rear wall 109.

As all the other illustrated embodiments are in many ways similar in construction and operation to the first embodiment, for the sake of clarity not all features are repeated in the drawings, and the expert will have no difficulty in determining where they are required.

Figure 2:
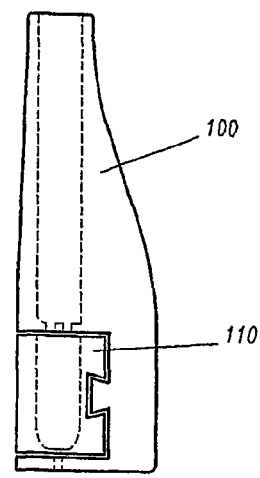
Figure 3:
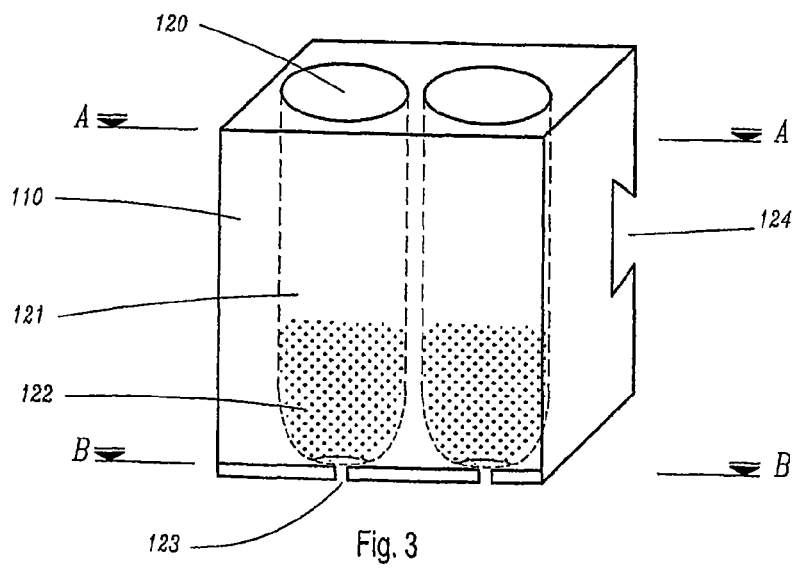
FIG. 3 is a perspective view of a powder cartridge as used in the Tray model.

As shown in FIG. 1, the inhaler body 100 has a rail 104 which guides and holds in place a powder cartridge 110, shown in more detail in FIG. 3, in the manner shown in FIG. 2. As can be seen from FIGS. 2 and 3, the powder cartridge 110 has a rail guide 124 formed on its back surface which is of complementary size and shape to the rail 104, the interface between the rail and guide restricting the cartridge to a transverse sliding movement across the body opening 102.

As shown in FIG. 3, the powder cartridge 110, used in a Tray model, includes two identical powder compartments 121. The compartments 121 are shown only partially filled with powder 122, but they can be filled to full capacity if required, depending upon the characteristics of the powder. Powders with poor flow properties will require free space inside the compartment 121 to become fully aerosolized, whereas free flowing powders are more permeable to air and will become entrained and flow out of the compartment even when it is full. Each compartment 121 is provided in its front face with an compartment front inlet 120, through which the powder will flow when a suction is applied to mouthpiece 103 with the compartment 121 aligned with body front inlet 105. In order to enable air to enter the compartment 121 so as to create a through-flow when this suction is applied, each compartment 121 also includes a compartment rear inlet 123 in the rear face of the cartridge 110, which must be aligned with body rear inlet 106 for fluid communication to be established. More air is supplemented to the inhalation flow through body side inlets 130 and 131, which extend from the inhaler body 100 to the mouthpiece channel 103 (see FIG. 6), immediately above the body front inlet 105.

Figure 4:
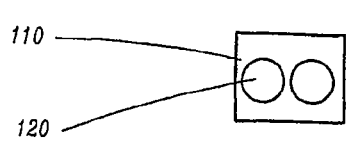
FIGS. 4 and 5 are front and rear elevations, respectively, of a powder cartridge as used in the Tray model.
Figure 5:
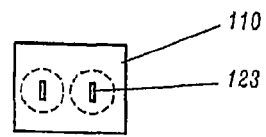

FIGS. 4 and 5 show elevations of the powder cartridge 110. The front elevation in FIG. 4 (from section AA in FIG. 3) displays a front inlet 120 of a compartment, which will adjoin front wall 108 and face the body front inlet 105 in the inhalation position. The rear elevation in FIG. 5 (from section BB in FIG. 3) shows a rear inlet 123 of a compartment, which will adjoin the rear wall 109, each of which admits air into its associated compartment 121 so that the air can pass through the powder contained therein, each compartment rear inlet 123 being shaped as a very narrow slit, to prevent powder from leaking during powder filling. The rail guide 124 is characteristic of the powder cartridge 110 used in a Tray model, and is absent in the powder compartment of Shuttle or Split Tray model embodiments described hereinafter, where the walls of the powder cartridge 110 can be smooth. A detent is provided on one of the walls of the powder cartridge 110 and on the adjoining area of one of the walls of the opening 102 (neither shown) in the Tray model, giving an audible or tactile sign to the user of the inhaler at the precise positions of inhalation. Moreover, models Shuttle, Split-Tray, Cylinder and Disk can be provided with means to prevent the user from overshooting the inhalation position.

Figure 23:
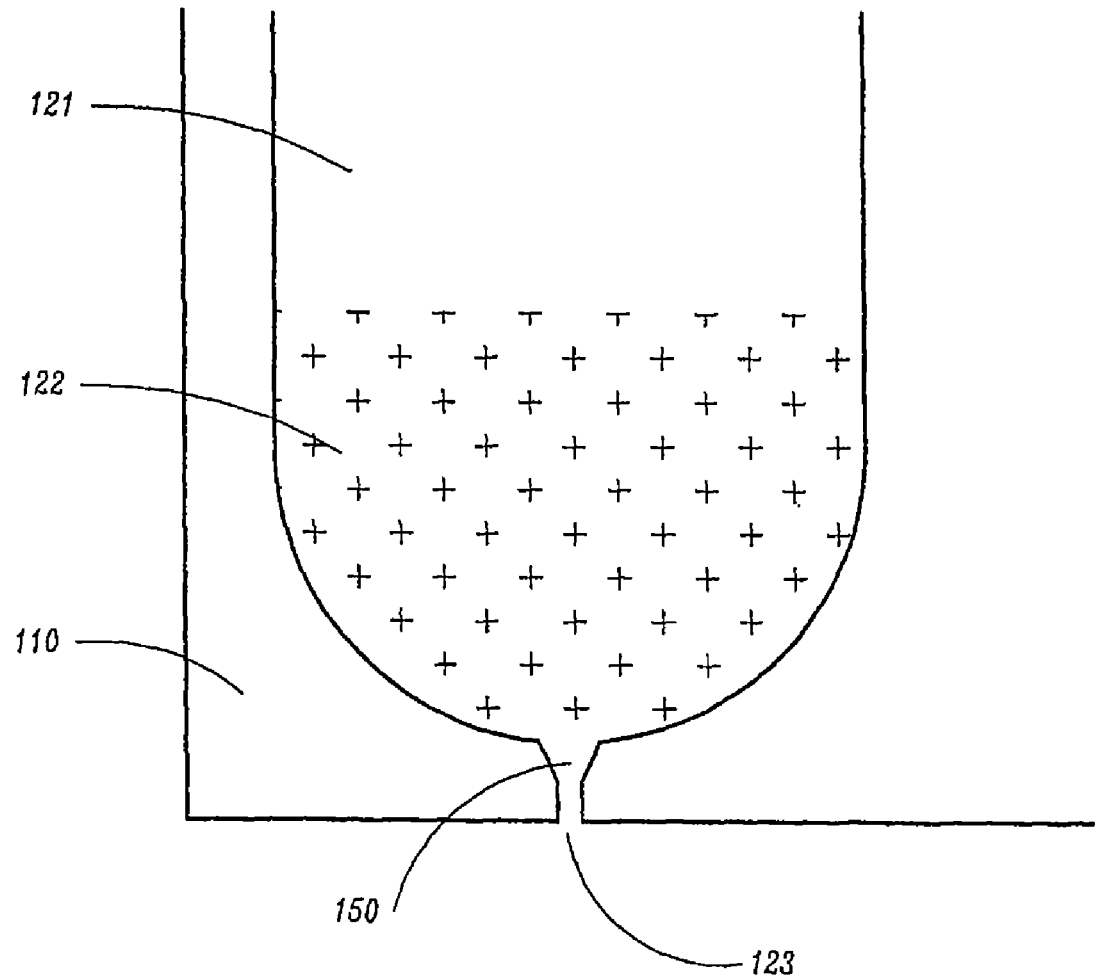
FIG. 23 is a longitudinal section of a detail of a powder compartment.

FIG. 23 is a detailed section view of a powder cartridge 110 which can be used in the Tray model, but in all other embodiments as well. The walls of compartment rear inlet 123 are parallel at first, but then begin to taper out, to form a funnel 150, the objective of which is to promote the bridging of the powder 122 above the funnel 150, or to allow the powder 122 to enter the funnel and to plug it. In both cases the objective is to prevent any leaking of powder out of compartment rear inlet 123.

Figure 6:
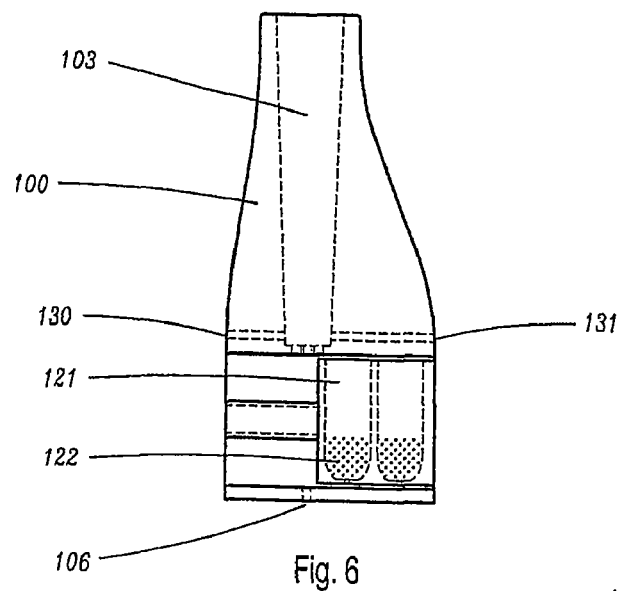
FIGS. 6, 7 and 8 are plans views of the Tray model in operation.
Figure 7:
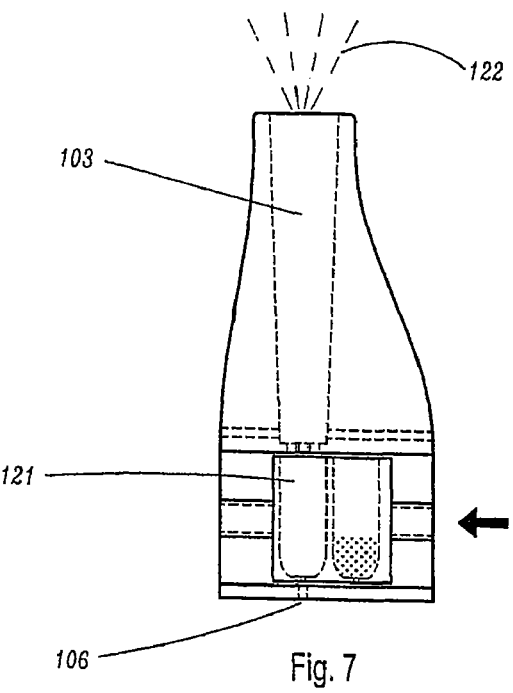
Figure 8:
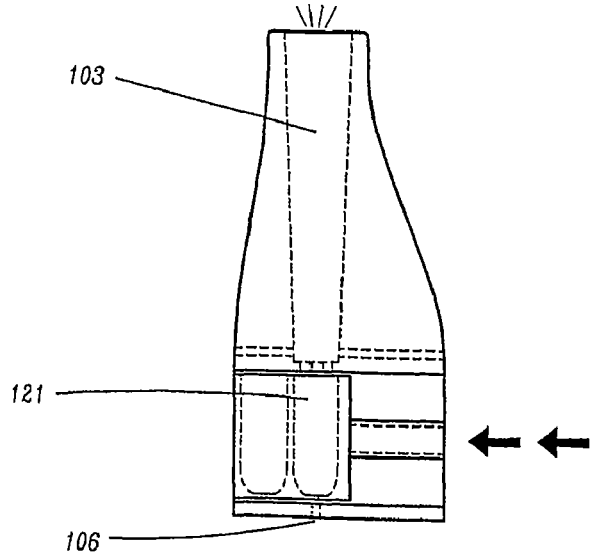

Referring next to FIGS. 6, 7 and 8, there is shown the Tray model in three different operational configurations. In FIG. 6, the powder cartridge 110 is in its storage position with the compartment front inlet 120 of each powder compartment 121 offset from the body front inlet 105 and of the mouthpiece 103 and closed off by the smooth walls 108 and 109 of inhaler body 100 so that the powder 122 is blocked inside the compartment 121. In FIG. 7, the powder cartridge 110 has been advanced from the storage position shown in FIG. 6 to a first use position in which one of the powder compartments 121 is aligned with the mouthpiece 103, establishing fluid communication between body rear inlet 106 and compartment 121, enabling inhalation of the powder contained therein to take place.

Continued advancement of the cartridge 110 from the first use position shown in FIG. 7 brings the cartridge onto a second use position in which the other powder compartment 121 is brought into alignment with mouthpiece 103, so as to enable inhalation of the powder contained therein to take place.

Figure 9:
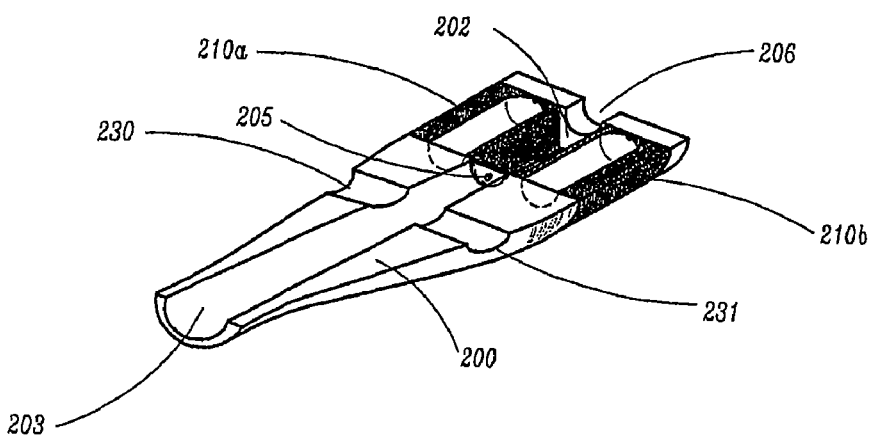
FIGS. 9, 10 and 11 are perspectives of section views of the Split Tray model in operation.
Figure 10:
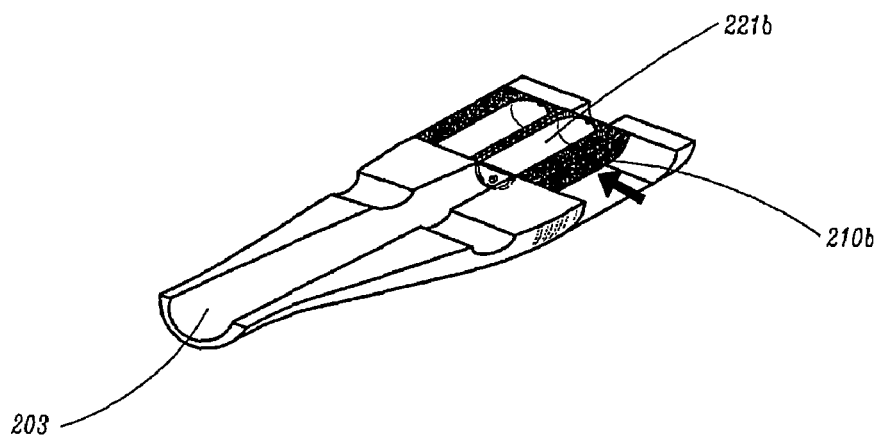
Figure 11:
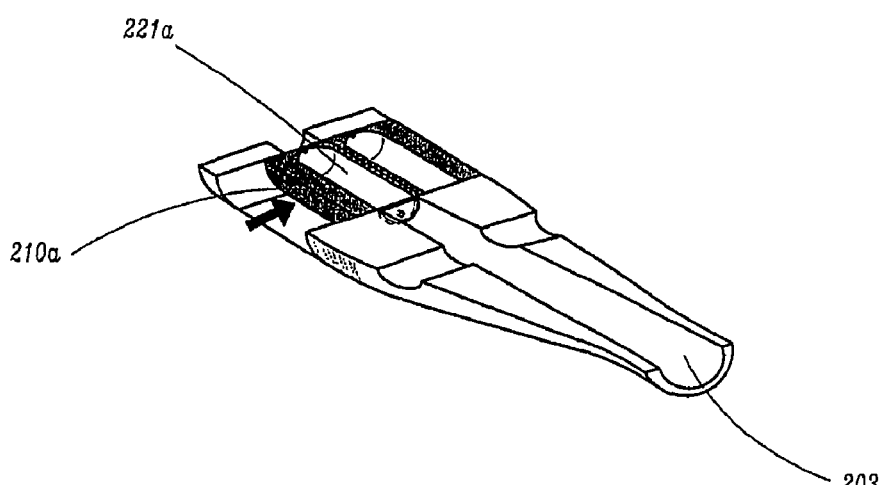
Figure 16:
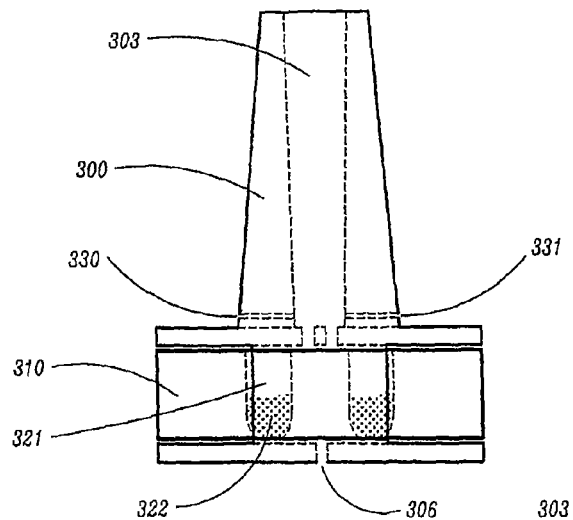
FIGS. 16, 17 and 18 are plan views of the Shuttle model in operation.
Figure 17:
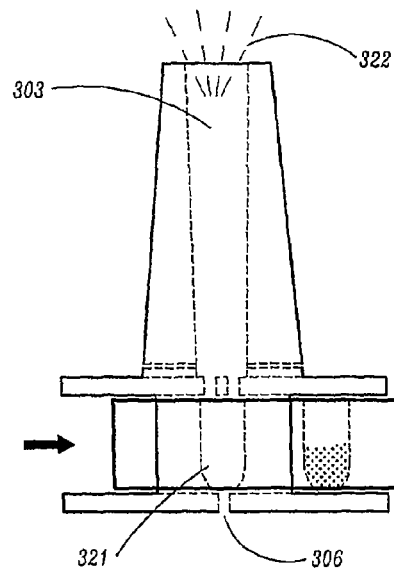
Figure 18:
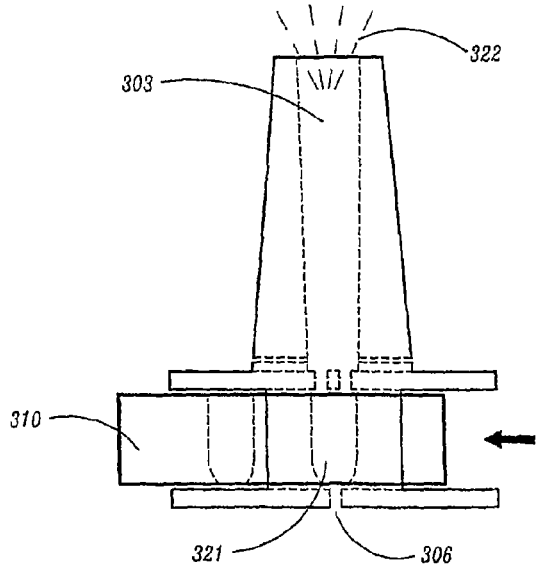
Figure 19:
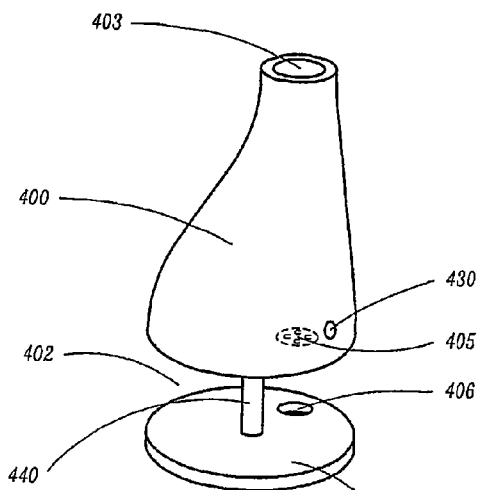
FIGS. 19 and 20 are perspective views of an inhaler body and a powder cartridge respectively, according to a further embodiment known as a Cylinder model.
Figure 20:
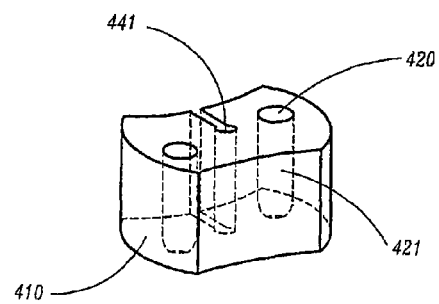
Figure 21:
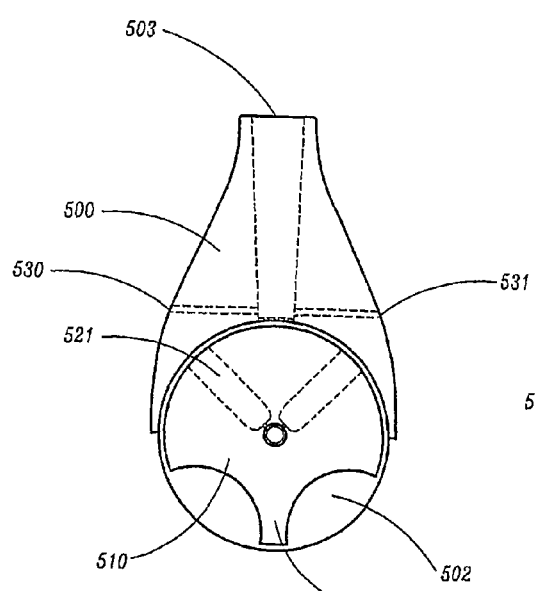
FIG. 21 is a longitudinal section of a still further embodiment of the invention referred to as a Disk model.
Figure 22:
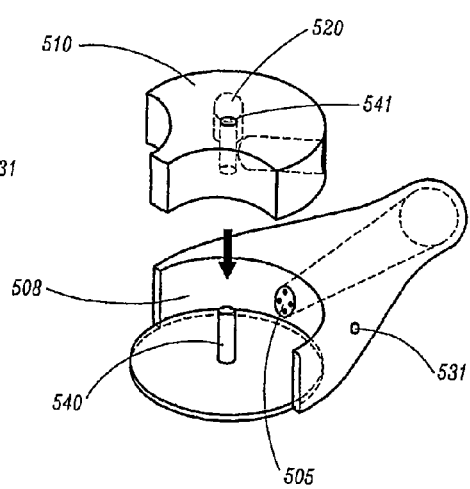
FIG. 22 is a perspective view of an inhaler body and of a powder cartridge of the Disk model.

Referring next to FIGS. 9, 10 and 11, these show a perspective of a longitudinal section of the inhaler body in operation, according to a second embodiment of the invention hereinafter referred to as a Split Tray model. As with the first embodiment, the Split Tray model has an inhaler body 200, a mouthpiece 203 which extends to body front inlet 205 and which is in communication with body side inlets 230 and 231. For clarity purposes, the body side inlets have been drawn farther from body front inlet 205 than is desirable. A rear body inlet 206 is again provided at the bottom of the inhaler body 200, aligned with the longitudinal axis of the mouthpiece 203 and body front inlet 205.

The Split Tray model, unlike the other embodiments, has two powder cartridges 210a, 210b, which are separately formed from each other, each including just a single compartment. FIG. 9 shows the Split tray model in its storage position in which both cartridges are offset from the body front inlet 205 of the mouthpiece—the compartments 221a, 221b of each cartridge 210a, 210b being engaged with the smooth walls of inhaler body 200 so that the powder is sealed inside the compartments 22Ia$_5$ 221b. From the storage position of FIG. 9, a first inhaling configuration is achieved by advancing one of the powder cartridges 210b into the inhaler body 200 as shown in FIG. 10 so as to bring the compartment 221b into alignment with the mouthpiece 203, thereby enabling inhalation to take place. A second inhaling configuration is then achieved by advancing the other powder cartridge 210*a* into the inhaler body 200 in the opposite direction, pushing the now empty powder cartridge 210*b* away from the inhalation position and in turn bringing the still powder loaded compartment 221*a* of the other cartridge in turn in alignment with the mouthpiece 203. Inhalation of the powder in the other cartridge can then take place.

Referring next to FIG. 12, there is shown a longitudinal section of the inhaler body according to a third embodiment of the present invention, hereinafter referred to as the Shuttle model. As with the previous embodiments, the Shuttle model has an inhaler body 300, a mouthpiece 303 which extends to body front inlet 305, body side inlets 330, 331, a front wall 308 and a rear wall 309. A body rear inlet 306 is again provided a the bottom of the inhaler body 300, aligned with the longitudinal axis of the mouthpiece 303.

FIG. 13 is a transversal section of the Shuttle (or Split Tray) model, which shows more clearly the opening 302 which is designed to hold a powder cartridge. FIG. 14 is a front elevation of the inhaler body 300 (200) used in a Shuttle (or Split Tray) model, showing a mouthpiece 303, and inside it, a view of the body front inlet 305 which admits air and powder to the mouthpiece 303.

FIG. 15 is a rear elevation of the inhaler body 300 (200), used in the same models, showing here a single body rear inlet 306 to admit air to a powder compartment. As can be seen from these views, the Shuttle model does no include a rail on the body or a rail guide on the cartridge in difference to the first embodiment.

FIGS. 16, 17 and 18 show the operational positions of the Shuttle model. In FIG. 16, the powder cartridge 310 is in its storage position with the powder compartments 321 offset from the mouthpiece 303 and from the body rear inlet 306, the inlets of compartment 321 instead being sealed off through engagement with the smooth front 308 and rear 309 walls, so that the powder 322 is blocked inside the compartment 321. In FIG. 17, the powder cartridge 310 has been advanced to a first inhaling position in which the powder compartment 321 is aligned with the body rear inlet 306 and with mouthpiece 303, thereby enabling inhalation of the powder 322 of the first compartment to take place. In FIG. 18, the powder cartridge 310 has been advanced in the opposite direction, moving the cartridge back through its storage position and continuing, so that the other compartment 321 is aligned with the mouthpiece 303, enabling inhalation of the second compartment to take place. Unlike the Tray model, in the case of the Shuttle model the user does not have to take particular care at stopping a powder compartment 321 at a precise inhalation position, and only needs to push the powder cartridge 310 as far as it will go for proper alignment to be achieved.

A fourth embodiment is shown in FIGS. 19 and 20. FIG. 19 is a perspective view of a rotary actuated inhaler body which operates in conjunction with a cylinder powder cartridge 410, which will hereinafter be referred to as the Cylinder model. The difference in relation to the previous embodiments is that the powder cartridge 410 is provided with an opening 441 by means of which it is journal mounted on an inhaler body axle 440 which extends perpendicularly to the longitudinal axis of the mouthpiece so as to enable the cartridge 410 to be rotated relative to the inhaler body 400 in order to bring the powder compartments 420 into inhalation alignment with the mouthpiece 403. The spindle 440 is hollow and is provided with an inlet (not shown), so that as in all other models, air can flow through each powder compartment 421 and into the mouthpiece 403. The passage of air through the inhaler is established in substantially the same way as with the Tray, Shuttle and Split Tray models, aligning the compartment front inlet 420 with the mouthpiece channel 403 so as to allow an air flow path through each compartment 421, and the user turns the powder cartridge 410 first to one side, as far as it will go, to bring one of the compartments into alignment with the mouthpiece 403 and inhale, and then repeat the action in the opposite direction to inhale the powder from the second compartment.

FIG. 21 shows a longitudinal section of an inhaler body 500 assembled with a cartridge 510 according to a fifth embodiment of the invention, hereinafter referred to as the Disk model and FIG. 22 shows a corresponding perspective view. Here the powder cartridge 510 is formed as a disk, the inhaler body opening being a complementary shape to receive the cartridge 510, and the powder compartments 521 being positioned at a 90° angle in relation to each other. The powder cartridge 510 is further provided with a finger grip 542, which the user moves from side to side to bring each powder compartment 521 in alignment with the inlet 505 and the mouthpiece 503.

The operation of the Cylinder and Disk models is analogous to that of the other models, the user rotating the powder cartridge 410; 510 in one direction and then the other, to bring each powder compartment 410; 510 in alignment with mouthpiece 403; 503. In storage, the powder compartment 421; 521 is prevented from spilling by a close contact with the smooth front and rear walls, of which can be seen rear wall 409 in FIG. 19 and front wall 509 in FIG. 22.

FIG. 23 shows a detail of a powder compartment 121, which can be incorporated into the cartridge 110 of all the above described embodiments. The compartment rear inlet 123 takes the shape of a funnel 150 which helps to promote the bridging of the powder 122 and reduce the probability of leakage during filling.

An inhaler embodiment of the present invention has been tested to determine its aerodynamic profile as well as its powder dose delivery characteristics compared to another marketed dry-powder inhaler, FlowCaps® (Hovione SA Lisbon, Portugal).

The procedure to measure the pressure drop across the inhaler at a given airflow is described in the European Pharmacopoeia. A Shuttle model prototype was used for this test and the pressure drop across the device was found to be identical to that of FlowCaps, 4.0 kPa when a flow of 35 $L/min^{-1}$ was applied.

An experimental anti-viral compound was then formulated to determine the dispersion and the entrainment efficacy of both devices. The active ingredient was previously micronized using a conventional jet-mill and particle sizes were achieved where more than 50% of the particles had a diameter smaller than 5 μm, as measured by laser diffraction (Malvern, UK). The active drug was formulated in batches of 1, 5 and 7.5 mg of drug per 25 mg of drug powder blend, where the difference was made up by adding lactose. Two grades of lactose were used, DMV SV003 (“coarse” lactose) and Pharmatose 450M (“fine” lactose), both from DMV (Holland). Instead of lactose, other choices could have been glucose, saccharose, maltose, mannitol, sorbitol, xylitol or dextran, individually or in combination, which are known to be advantageous in powder inhalation formulations.

After blending of the blend components to produce an ordered mix and determining the batch homogeneity, the formulated powder was filled into cellulose capsules, size 4, (Shionogi, Japan) for use with FlowCaps, and into powder compartments, for use with the Shuttle prototype. The inhalers were then tested at a flow rate of 35 $L/min^{-1}$ on an Andersen cascade impactor (Graseby Andersen, Smyrna, Ga.), actuated twice to allow a volume of 2×2 liters of air to pass through the device, and the mass of active drag deposited at each stage of the cascade impactor was quantified using high pressure liquid chromatography. From these data, the emitted dose and the fine particle dose were calculated, where the emitted dose was the sum of all drug masses collected from each of the impactor stages, including the inductor throat, and the fine particle dose was the mass of drug collected below the 5 μm cutoff point. The ratio of the fine particle dose to the emitted dose is the fine particle fraction and is a measure of inhaler efficiency. The higher the fine particle dose, the higher the lung dose is expected to be. The results are summarized in the following table:

The data indicate that both inhalers have a comparable performance in terms of fine particle dose, correlating well with the particle size of the micronized active drug, and demonstrate that inhalers of the present invention are suitable for the delivery of large doses of pharmaceutical active ingredients, pre-metered directly into the inhaler, without a primary container such as a capsule or a blister. This results in an inhaler which is more economical and simpler to use, without sacrificing performance.

The person skilled in the art will recognize in this performance an ability of the present inhaler to deliver other types of drugs, namely beta2-agonists, anticholinergics, corticosteroids, analgesics, antibiotics, vaccins, proteins, peptides and insulin and other drugs deliverable by inhalation.

The invention claimed is:

1. A dry powder inhaler suitable for pulmonary or nasal delivery, comprising:
   (a) an inhaler body having a mouthpiece, an opening in the body, and a body front inlet extending from the mouthpiece to the opening in the body for providing fluid communication therebetween; and
   (b) a cartridge movably mounted in the opening in the body and having at least one powder compartment formed therein which includes a compartment front inlet;
   the cartridge being movable relative to the inhaler body between at least a first position in which the compartment front inlet of the at least one powder compartment is offset from the body front inlet so as to isolate the contents of the powder compartment from the mouthpiece, and a second position in which the compartment front inlet of the at least one powder compartment is aligned with the body front inlet;
   each of the inhaler body and the cartridge being of unitary construction such that the inhaler is formed of only two separate parts which are moveable relative to each other; and
   the cartridge being a close tolerance fit in the opening in the body such that in the first position of the cartridge, the compartment front inlet is closed by the body so as to prevent the contents escaping therefrom;
   the inhaler body further includes a body rear inlet extending therethrough to the opening in the inhaler body and each powder compartment further includes a compartment rear inlet, wherein, in the first position of the cartridge, the compartment rear inlet is closed by the body so as, in use, to prevent the contents of the compartment from escaping therefrom, and in the second position of the cartridge, the compartment rear inlet aligns with the body rear inlet so as to create an air flow path through the compartment to the mouthpiece, such that the compartment forms a dispersion chamber for delivering the contents of the compartment to the mouthpiece.

2. A dry powder inhaler according to claim 1, characterized by the compartment rear inlet being sized so as substantially to prevent the powder from passing therethrough and out of the compartment under gravity during filling, and said compartment rear inlet has at least one dimension which is 1 mm or less.

3. A dry powder inhaler according to claim 2, characterized by the compartment rear inlet comprises a funnel portion tapering outwardly towards the compartment front inlet.

4. A dry powder inhaler according to claim 3, characterized in that the taper angle of the funnel is in the range of between 179° and the angle of repose of a pharmaceutical powder used.

5. A dry powder inhaler according to claim 1, characterized by the body having body side inlets disposed between said body front inlet and an end of the mouthpiece distant from the body front inlet.

6. A dry powder inhaler according to claim 5, characterized by the inhaler body further including obstructions disposed to prevent blocking the passage of air through the body rear inlet and body side inlets by the hand of a user.

7. A dry powder inhaler according to claim 1, characterized by the cartridge being in a close tolerance fit in the opening in the body such that when the compartment front and rear inlets of a powder compartment are offset from the body front and rear inlets, the inhaler body substantially sealingly engages the front and rear compartment inlets thereof so as to prevent powder leaking from said compartment.

8. A dry powder inhaler according to claim 1, characterized by the body front inlet in combination with a powder compartment defines a powder dispersion area and reduces the flow of air leaving said powder compartment and entering said mouthpiece.

9. A dry powder inhaler according to claim 1, characterized by the opening in the inhaler body extends transversally to the inhaler body and the cartridge is slidably moveable along the opening transverse to the inhaler body, the longitudinal axis of each compartment being oriented parallel to the longitudinal axis of the mouthpiece.

10. A dry powder inhaler according to claim 1, characterized by the cartridge being rotatably engageable in the opening.

11. A dry powder inhaler according to claim 10, characterized by the cartridge being cylindrically shaped and rotates in the opening about an axis parallel to the longitudinal axis of a mouthpiece passage.

12. A dry powder inhaler according to claim 10, characterized by the cartridge being disk shaped and rotates in the opening about an axis substantially perpendicular to the longitudinal axis of a mouthpiece passage.

13. A dry powder inhaler according to claim 1, characterized by the cartridge being advanced to bring the compartment front inlet into fluid communication with the body front inlet with a single movement of the cartridge.

14. A dry powder inhaler according to claim 1, characterized by the cartridge includes at least two powder compartments which are isolated from each other.

15. A dry powder inhaler according to claim 14, characterized by a first block disposed to prevent movement of the cartridge in a first direction beyond the point where the compartment front inlet of one of said compartments is in fluid communication with the body front inlet, and a second block disposed to prevent movement of said cartridge in a direction contrary to the first direction beyond the point where the compartment front inlet of the second compartment is in fluid communication with said body front inlet.

16. A dry powder inhaler according to claim 1 which includes just a single cartridge, where each of the inhaler body and said cartridge are formed as a unitary part, such that the inhaler is composed of just two parts.

17. A dry powder inhaler according to claim 3, characterized in that the taper angle of the funnel is in the range of between 120° and the angle of repose of a pharmaceutical powder used.

18. A dry powder inhaler according to claim 17, characterized in that the compartment rear inlet is in the form of a slit.

19. A dry powder inhaler according to claim 18, characterized by the cartridge being in a close tolerance fit in the opening in the body such that when the compartment front and rear inlets of a powder compartment are offset from the body front and rear inlets, the inhaler body substantially sealingly engages the front and rear compartment inlets thereof so as to prevent powder leaking from said compartment.

20. A dry powder inhaler according to claim 19, characterized by the body having body side inlets disposed between said body front inlet and an end of the mouthpiece distant from the body front inlet.

21. A dry powder inhaler according to claim 20, characterized by the fact that the body front inlet in combination with a powder compartment defines a powder dispersion area and reduces the flow of air leaving said powder compartment and entering said mouthpiece.

22. A dry powder inhaler according to claim 21, characterized by the inhaler body further including obstructions disposed to prevent blocking the passage of air through the body rear inlet and body side inlets by the hand of a user.

23. A dry powder inhaler according to claim 21, characterized by the cartridge includes at least two powder compartments which are isolated from each other.

24. A dry powder inhaler according to claim 23, characterized by a first block disposed to prevent movement of the cartridge in a first direction beyond the point where the compartment front inlet of one of said compartments is in fluid communication with the body front inlet, and a second block disposed to prevent movement of said cartridge in a direction contrary to the first direction beyond the point where the compartment front inlet of the second compartment is in fluid communication with said body front inlet.

25. A dry powder inhaler according to claim 21, characterized by the cartridge being rotatably engageable in the opening.

26. A dry powder inhaler according to claim 25, characterized by the cartridge being cylindrically shaped and rotates in the opening about an axis parallel to the longitudinal axis of a mouthpiece passage.

27. A dry powder inhaler according to claim 25, characterized by the cartridge being disk shaped and rotates in the opening about an axis substantially perpendicular to the longitudinal axis of a mouthpiece passage.

* * * * *